United States Patent
Jennewein

(10) Patent No.: US 11,582,994 B2
(45) Date of Patent: Feb. 21, 2023

(54) SPRAY-DRIED 3-FUCOSYLLACTOSE

(71) Applicant: Chr. Hansen HMO GmbH, Rheinbreitbach (DE)

(72) Inventor: Stefan Jennewein, Bad Honnef (DE)

(73) Assignee: Chr. Hansen HMO GmbH, Rheinbreitbach (DE)

( * ) Notice: Subject to any disclaimer, the term of this patent is extended or adjusted under 35 U.S.C. 154(b) by 0 days.

(21) Appl. No.: 16/770,224

(22) PCT Filed: Dec. 7, 2018

(86) PCT No.: PCT/EP2018/083969
§ 371 (c)(1),
(2) Date: Jun. 5, 2020

(87) PCT Pub. No.: WO2019/110801
PCT Pub. Date: Jun. 13, 2019

(65) Prior Publication Data
US 2021/0171992 A1    Jun. 10, 2021

(30) Foreign Application Priority Data

| Dec. 8, 2017 | (EP) | ................................. | 17206124 |
| Dec. 8, 2017 | (EP) | ................................. | 17206159 |
| Dec. 8, 2017 | (EP) | ................................. | 17206223 |
| Dec. 11, 2017 | (EP) | ................................. | 17206414 |
| Feb. 8, 2018 | (EP) | ................................. | 18155669 |

(51) Int. Cl.

| A23L 33/125 | (2016.01) |
| A23L 33/135 | (2016.01) |
| A23L 33/00 | (2016.01) |
| A23P 10/40 | (2016.01) |
| A23C 9/20 | (2006.01) |
| A23L 3/46 | (2006.01) |
| B01D 9/00 | (2006.01) |
| B01D 61/02 | (2006.01) |
| B01D 61/14 | (2006.01) |
| B01D 61/42 | (2006.01) |
| C07H 1/06 | (2006.01) |
| C07H 3/06 | (2006.01) |
| A23L 5/20 | (2016.01) |
| A61K 35/741 | (2015.01) |
| A61K 47/26 | (2006.01) |
| B01D 61/58 | (2006.01) |
| A23L 33/18 | (2016.01) |
| C12N 9/12 | (2006.01) |
| A23L 29/00 | (2016.01) |
| C07H 1/00 | (2006.01) |
| C12P 17/18 | (2006.01) |
| C12P 19/00 | (2006.01) |

(52) U.S. Cl.
CPC ............ *A23L 33/125* (2016.08); *A23C 9/206* (2013.01); *A23L 3/46* (2013.01); *A23L 5/273* (2016.08); *A23L 29/065* (2016.08); *A23L 33/135* (2016.08); *A23L 33/18* (2016.08); *A23L 33/40* (2016.08); *A23P 10/40* (2016.08); *A61K 35/741* (2013.01); *A61K 47/26* (2013.01); *B01D 9/005* (2013.01); *B01D 9/0018* (2013.01); *B01D 61/027* (2013.01); *B01D 61/145* (2013.01); *B01D 61/422* (2013.01); *B01D 61/58* (2013.01); *C07H 1/00* (2013.01); *C07H 1/06* (2013.01); *C07H 3/06* (2013.01); *C12N 9/12* (2013.01); *C12P 17/181* (2013.01); *C12P 19/00* (2013.01); *A23V 2002/00* (2013.01); *B01D 2009/0086* (2013.01); *B01D 2311/02* (2013.01); *B01D 2311/2623* (2013.01); *B01D 2311/2626* (2013.01)

(58) Field of Classification Search
None
See application file for complete search history.

(56) References Cited

U.S. PATENT DOCUMENTS

| 2011/0300584 A1 | 12/2011 | Hufner et al. |
| 2014/0024820 A1 | 1/2014 | Parkot et al. |
| 2015/0183814 A1 | 7/2015 | Schroven et al. |
| 2016/0237104 A1 | 8/2016 | Jennewein et al. |
| 2016/0333042 A1 | 11/2016 | Jennewein |
| 2019/0177352 A1 | 6/2019 | Jennewein |
| 2019/0292211 A1 | 9/2019 | Jennewein et al. |
| 2019/0382737 A1 | 12/2019 | Hüfner et al. |

FOREIGN PATENT DOCUMENTS

| CN | 102154163 A | 8/2011 |
| CN | 102858191 A | 1/2013 |
| CN | 103501639 A | 1/2014 |
| CN | 103763940 A | 4/2014 |
| CN | 104822279 A | 8/2015 |
| CN | 104955344 A | 9/2015 |

(Continued)

OTHER PUBLICATIONS

International Search Report for Application No. PCT/EP2018/083969 dated Dec. 2, 2019.
Stephan Thurl, et al., "Systematic review of the concentrations of oligosaccharides in human milk," Nutrition reviews, (2017), vol. 75, No. 11: 920-933.
Gu, "Physiological function characteristic of milk and milk product," Saccharides in Milk, 2000, Chapter 3, 103-114.
Machine translation of CN102154163, Aug. 17, 2011, Zhu, 6 pages.
Machine translation of TW201249349, dated Dec. 16, 2012, Berrocal et al., 23 pages.

*Primary Examiner* — Christian L Fronda
(74) *Attorney, Agent, or Firm* — McNeill Baur PLLC

(57) ABSTRACT

Disclosed is a method for the manufacture of a spray-dried powder consisting essentially of 3-fucosyllactose, the spray-dried powder, its use for the manufacture of nutritional compositions, and nutritional compositions containing the spray-dried powder.

17 Claims, 3 Drawing Sheets

(56) References Cited

FOREIGN PATENT DOCUMENTS

| | | | |
|---|---|---|---|
| CN | 105532883 A | 5/2016 | |
| CN | 105722515 A | 6/2016 | |
| CN | 103797021 B | 8/2016 | |
| CN | 106255505 A | 12/2016 | |
| EP | 2896628 A1 | 7/2015 | |
| EP | 3111942 A1 | 1/2017 | |
| EP | 3450443 A1 | 3/2019 | |
| JP | 2017527311 A | 9/2017 | |
| TW | 201249349 A | 12/2012 | |
| WO | 2010070104 A1 | 6/2010 | |
| WO | 2011136647 A1 | 11/2011 | |
| WO | 2011150939 A1 | 12/2011 | |
| WO | 2012069415 A1 | 5/2012 | |
| WO | 2012092155 A1 | 7/2012 | |
| WO | 2012097950 A1 | 7/2012 | |
| WO | WO-2012112777 A2 * | 8/2012 | ............ C07H 13/04 |
| WO | 2012156273 A1 | 11/2012 | |
| WO | 2013185780 A1 | 12/2013 | |
| WO | 2014075680 A1 | 5/2014 | |
| WO | 2014086373 A1 | 6/2014 | |
| WO | 2014094783 A1 | 6/2014 | |
| WO | 2014100126 A1 | 6/2014 | |
| WO | 2014100191 A1 | 6/2014 | |
| WO | 2015049331 A1 | 4/2015 | |
| WO | 2015071389 A1 | 5/2015 | |
| WO | 2015106943 A1 | 7/2015 | |
| WO | 2015150328 A1 | 10/2015 | |
| WO | 2015164021 A1 | 10/2015 | |
| WO | 2016040531 A1 | 3/2016 | |
| WO | 2016086947 A1 | 6/2016 | |
| WO | 2017043382 A1 | 3/2017 | |
| WO | 2017101953 A1 | 6/2017 | |
| WO | 2017103019 A1 | 6/2017 | |

* cited by examiner

SPRAY-DRIED 3-FUCOSYLLACTOSE

CROSS-REFERENCE TO RELATED APPLICATIONS

This application is the National Stage entry of International Application No. PCT/EP2018/083969, filed 7 Dec. 2018, which claims priority to European Patent Application No. 18155669.7, filed 8 Feb. 2018, European Patent Application No. 17206414.9, filed 11 Dec. 2017, European Patent Application No. 17206223.4, filed 8 Dec. 2017, European Patent Application No. 17206159.0, filed 8 Dec. 2017, and European Patent Application No. 17206124.4, filed 8 Dec. 2017.

BACKGROUND

Field

The present invention relates to preparations of human milk oligosaccharide. More specifically, the present invention relates to solid preparations of human milk oligosaccharides and to methods for the manufacturing of said solid preparations of human milk oligosaccharides.

Description of Related Art

Human breast milk contains a substantial amount of carbohydrates. These carbohydrates include monosaccharides such as L-fucose and N-acetylneuraminic acid (Neu5Ac). The disaccharide lactose is also present in human breast milk. In addition to lactose, one liter of human breast milk contains up to 20 g/L oligosaccharides, the so-called "human milk oligosaccharides (HMOs)". HMOs represent the third most abundant constituent of human breast milk. It is presumed that more than 150 structurally distinct oligosaccharides are present in human milk. Human milk usually contains between 10 and 13 major HMOs which are present in a concentration of between grams to several hundred milligrams per liter (Thurl et al., (2017), Nutrition Reviews 75(11) 920-933). HMOs include neutral HMOs as well as acidic HMOs which contain one or more sialic acid moieties. The most prominent HMOs are shown in Table 1. The structural complexity and abundance of these oligosaccharides is unique for human milk and has not been found in the milk of other mammals such as—for example—domesticated dairy animals.

Since HMOs are not digested by humans, the physiological role of these saccharides is under investigation for several decades. The prebiotic effect of HMOs has been discovered over 100 years ago. HMOs are able to modulate the human gut microbiome by feeding beneficial bacteria. Several other functional effects of HMOs were investigated in the last years, especially their effect on neonates' development. HMOs are known to act as decoys to reduce the risk of infections by bacterial and viral pathogens, which adhere to human cells by binding to cell surface glycoproteins. Additionally, various HMOs possess an anti-inflammatory effect and act as immunomodulators. Hence, it was proposed that HMOs reduce the risks of developing food allergies. A positive effect of sialylated HMOs on neonatal brain development is intensely discussed (reviewed in "Prebiotics and Probiotics in Human Milk, Origins and functions of milk-borne oligosaccharides and bacteria", Academic Press (2017) editors: McGuire M., McGuire M., and Bode L.).

One HMO is 3-fucosyllactose (Gal($\beta$1-4)[Fuc($\beta$1-3)]Glc)). 3-Fucosyllactose (3-FL) was isolated for the first time from milk in 1958, and that was also isolated for the first time from the urine of a blood group O, non-secretor, woman during pregnancy and lactation in 1977. 3-Fucosyllactose is resistant to enzymic hydrolysis in the gastrointestinal tract of an infant. It is postulated that 3-fucosyllactose reaches the large intestine where it is internalized and metabolized by bacteria.

A first step to take advantage of the beneficially effects of HMOs for bottle-fed infants is the addition of individual HMOs to infant formula. However, supplementing infant formulae with a combination of structurally distinct HMOs would be better, because a combination of structurally distinct HMOs will have effects that are more similar to the effects of their original source, human milk, and which can not be caused by individual HMOs.

The limited supply of individual HMOs for supplementing infant formulae has first led to the development of chemical syntheses of HMOs, followed by biocatalytic approaches using purified enzymes. Today, fermentation of genetically-engineered bacterial cells is used to produce different HMOs in commercial scales (WO 2015/150328 A1, WO 2017/043382 A1, WO 2010/070104 A1, WO 2012/097950 A1).

The HMOs that are synthesized by the bacterial cells can be purified from the fermentation broth or cell lysate to obtain substantially pure preparations of the HMOs such that they can be used in human food, especially in infant food.

During its purification, the 3-fucosyllactose is usually present in form of a liquid process stream. Along with the purification, the concentration of 3-fucosyllactose in the process stream is increased. However, an aqueous solution of 3-fucosyllactose is very vulnerable for bacterial or fungal contamination. Therefore, it is preferred to provide the 3-fucosyllactose as a dry product having a low content of water such that microbial growth is impossible.

Typically, a saccharide is obtained in solid form by crystallization. Crystallization of individual HMOs has been described: for 3-fucosyllactose (WO 2014/075680 A), for 2'-fucosyllactose (WO 2011/150939 A), Di-fucosyllactose (WO 2016/086947 A), lacto-N-tetraose (WO 2017/101953 A), lacto-N-neotetraose (WO 2014/094783 A). Crystallization of HMOs involves the use of organic solvents such as alcohols, mainly ethanol or methanol, or organic acids such as glacial acetic acid. However, the use of organic solvents for crystallizing HMOs as last step in the process of obtaining the final product in solid form is not appropriate if the HMOs shall be used as food ingredients. In addition, organic solvents are harmful to the environment and to any individual handling them. Thus, the use of organic solvents requires occupational safety measures and appropriate disposal which renders the use of organic solvents to be costly. Therefore, crystallization of HMOs to provide the HMOs in solid form has to be considered a drawback in the production of HMOs in an industrial scale.

Therefore, a process is desired which provides HMOs, in particular 3-fucosyllactose, in solid form, which is applicable in industrial scale production of HMOs, and which does not involve the use of an organic solvent at the end of the purification scheme to provide a solid preparation of said HMO.

The problem is solved by a process for providing a powder consisting essentially of the purified HMO, wherein said method comprises spray-drying of an aqueous solution which contains the HMO.

SUMMARY

In a first aspect, a spray-dried powder is provided method is provided consisting essentially of 3-fucosyllactose.

In a second aspect, a process for the manufacture of a spray-dried powder consisting essentially of 3-fucosyllactose is provided.

In a third aspect, the use of the spray-dried powder consisting essentially of 3-fucosyllactose for the manufacture of a nutritional composition is provided.

In a fourth aspect, a nutritional composition containing the spray-dried powder consisting essentially of 3-fucosyllactose is provided.

DETAILED DESCRIPTION

Figure 1:
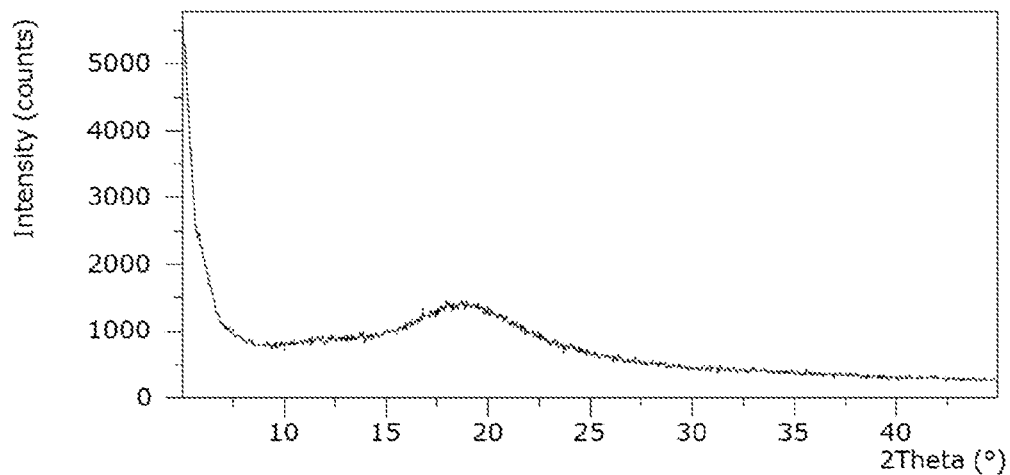
FIG. 1 shows a graph illustrating the results of a X-ray powder diffraction of spray-dried 3-fucosyllactose.

According to the first aspect, a spray-dried powder consisting essentially of 3-fucosyllactose produced by microbial fermentation is provided.

The 3-fucosyllactose is produced by microbial fermentation as described herein below. The term "consisting essentially of" as used herein, means that the spray-dried powder consists of 3-fucosyllactose and—optionally—by-products that are generated during the microbial fermentation for the production of the 3-fucosyllactose, but which could not have been removed from a process stream obtained from the microbial fermentation. The term "consisting essentially of" includes spray-dried powders consisting of at least 80%-wt., at least 85%-wt., at least 90%-wt., at least 93%-wt., at least 95%-wt. or at least 98%-wt. 3-fucosyllactose.

In an additional and/or alternative embodiment, the 3-fucosyllactose is present in the spray-dried powder in amorphous form.

In an additional and/or alternative embodiment, the spray-dried powder contains 15%-wt. of water, preferably ≤10%-wt. of water, more preferably ≤7%-wt. of water, most preferably ≤5%-wt. of water.

In an additional and/or alternative embodiment, the spray-dried powder is free of genetically-engineered microorganisms and nucleic acid molecules derived from genetically-engineered microorganisms.

According to the second aspect, provided is a process for the manufacture of a spray-dried powder consisting essentially of 3-fucosyllactose which has been produced by microbial fermentation. The process comprises the steps of:
a) purifying the 3-fucosyllactose from a fermentation broth;
b) providing an aqueous solution of the 3-fucosyllactose of step a); and
c) subjecting the solution of step b) to spray-drying.

In an additional and/or alternative embodiment, purifying the 3-fucosyllactose from fermentation broth includes one or more of the steps of:

i) removing the microbial cells from the fermentation broth to obtain a cleared process stream;
ii) subjecting the cleared process stream to at least one ultrafiltration;
iii) treating the cleared process stream at least one time with a cation exchange resin and/or at least one time with an anion exchange resin;
iv) subjecting the cleared process stream to at least one nanofiltration;
v) subjecting the cleared process stream to at least one electrodialysis;
vi) treating the cleared process stream at least one time with activated charcoal; and/or
vii) subjecting the cleared process stream at least one time to a crystallization and/or precipitation step.

The 3-fucosyllactose may be produced by microbial fermentation, wherein a genetically-engineered microorganism that is able to synthesize 3-fucosyllactose is cultivated in a culture medium (fermentation broth) and under conditions that are permissive for the synthesis of 3-fucosyllactose by said genetically-engineered microorganism. The purification of 3-fucosyllactose produced by microbial fermentation comprises the step of separating the microbial cells from the fermentation broth to obtain a cleared process stream which essentially free of cells and which contains the 3-fucosyllactose. This step is the first step in the process of purifying the desired oligosaccharides.

Suitable methods for separating the microbial cells from the fermentation broth include centrifugation wherein the microbial cells are obtained as a pellet and the fermentation broth as a supernatant. In an additional and/or alternative embodiment, the microbial cells are separated from the fermentation broth by means of filtration. Suitable filtration methods for separating the cells from the fermentation broth include microfiltration and ultrafiltration.

Microfiltration as such is a physical filtration process where a particle-containing fluid is passed through a special pore-sized membrane to separate the particles from the fluid. The term "microfiltration" as used herein refers to a physical filtration process where cells are separated from the fermentation broth.

Ultrafiltration is a variety of membrane filtration and is not fundamentally different. In ultrafiltration, forces like pressure or concentration gradients lead to a separation through a semipermeable membrane. Cells, suspended solids and solutes of high molecular weight are retained in the so-called retentate, while water and low molecular weight solutes such as the desired sialylated oligosaccharide pass through the membrane in the permeate (filtrate).

Ultrafiltration membranes are defined by the molecular weight cut-off (MACON) of the membrane used. Ultrafiltration is applied in cross-flow or dead-end mode.

Typically, the microbial cells synthesize the 3-fucosyllactose intracellularly and secrete it into the fermentation broth. The thus produced 3-fucosyllactose ends up in the fermentation broth which is then subjected to further process steps for the purification of the 3-fucosyllactose as described herein after.

Notwithstanding that the process is used for the purification of 3-fucosyllactose that has been produced by microbial fermentation, said process may also be employed to purify 3-fucosyllactose that was produced by enzymatic catalysis in-vitro. The 3-fucosyllactose can be purified from the reaction mixture at the end of the biocatalytic reaction. Said reaction mixture is subjected to the process for the purification as cleared process stream.

The cleared process stream contains the 3-fucosyllactose as well as a by-products and undesired impurities such as—for example—monosaccharides, disaccharides, undesired oligosaccharide by-products, ions, amino acids, polypeptides, proteins and/or nucleic acids.

In an additional and/or alternative embodiment, the process for the purification of 3-fucosyllactose comprises the step of at least one cation exchange treatment to remove positively charged compounds from the cleared process stream.

Suitable cation exchange resins for removing positively charged compounds include Lewatit S2568 ($H_+$) (Lanxess AG, Cologne, DE).

In an additional and/or alternative embodiment, the process for the purification of 3-fucosyllactose comprises the step of an anion exchange treatment to remove undesired negatively charged compounds from the cleared process stream.

Suitable anion exchange resins include Lewatit S6368 A, Lewatit S4268, Lewatit S5528, Lewatit 56368A (Lanxess AG. Cologne, DE), Dowex AG 1x2 (Mesh 200-400), Dowex 1x8 (Mesh 100-200), Purolite Chromalite CGA100x4 (Purolite GmbH, Ratingen, DE), Dow Amberlite FPA51 (Dow Chemicals, MI, USA).

In as additional/or alternative embodiment, the process for the purification of 3-fucosyllactose comprises a nanofiltration and/or a diafiltration step to remove impurities having a lower molecular weight, and to concentrate the desired oligosaccharides.

Diafiltration involves the addition of fresh water to a solution in order to remove (wash out) membrane-permeable components. Diafiltration can be used to separate components on the basis of their molecular size and charge by using appropriate membranes, wherein one or more species are efficiently retained and other species are membrane permeable. In particular, diafiltration using a nanofiltration membrane is effective for the separation of low molecular weight compounds like small molecule and salts. Nanofiltration membranes usually have a molecular weight cut-off in the range 150-1000 Daltons. Nanofiltration is widely used in the dairy industry for the concentration and demineralization of whey.

Suitable membranes for nanofiltration and/or diafiltration include Dow Filmtec NF270-4040, Trisep 4040-XN45-TSF (Microdyn-Nadir GmbH, Wiesbaden, DE), GE4040F30 and GH4040F50 (GE Water & Process Technologies, Ratingen, DE).

Diafiltration using nanofiltration membranes was found to be efficient as a pretreatment to remove significant amounts of contaminants prior to electrodialysis treatment of the solution containing the oligosaccharide. The use of nanofiltration membranes for concentration and diafiltration during the purification of HMOs results in lower energy and processing costs, and better product quality due to reduced thermal exposure, leading to reduced Maillard reactions and aldol reactions.

In an additional and/or alternative embodiment, the process for the purification of 3-fucosyllactose comprises at least one electrodialysis step.

Electrodialysis (ED) combines dialysis and electrolysis and can be used for the separation or concentration of ions in solutions based on their selective electromigration through semipermeable membranes.

The basic principle of electrodialysis consists of an electrolytic cell comprising a pair of electrodes submerged into an electrolyte for the conduction of ions, connected to a direct current generator. The electrode connected to the positive pole of the direct current generator is the anode, and the electrode connected to the negative pole is the cathode. The electrolyte solution then supports the current flow, which results from the movement of negative and positive ions towards the anode and cathode, respectively. The membranes used for electrodialysis are essentially sheets of porous ion-exchange resins with negative or positive charge groups, and are therefore described as cationic or anionic membranes, respectively. The ion-exchange membranes are usually made of polystyrene carrying a suitable functional group (such as sulfonic acid for cationic membranes or a quaternary ammonium group for anionic membranes) cross-linked with divinylbenzene. The electrolyte can be, for example, sodium chloride, sodium acetate, sodium propionate or sulfamic acid. The electrodialysis stack is then assembled in such a way that the anionic and cationic membranes are parallel as in a filter press between two electrode blocks, such that the stream undergoing ion depletion is well separated from the stream undergoing ion enrichment (the two solutions are also referred to as the diluate (undergoing ion depletion) and concentrate (undergoing ion enrichment). The heart of the electrodialysis process is the membrane stack, which consists of several anion-exchange membranes and cation-exchange membranes separated by spacers, installed between two electrodes. By applying a direct electric current, anions and cations will migrate across the membranes towards the electrodes.

In an additional and/or alternative embodiment, the process for the purification of 3-fucosyllactose further comprises a step of continuous chromatography like simulated bed moving (SMB) chromatography.

Simulated moving bed (SMB) chromatography originated in the petrochemical and mineral industries. Today, SMB chromatography is used by the pharmaceutical industry to isolate enantiomers from racemic mixtures. Large-scale SMB chromatography has already been used for the separation of the monosaccharide fructose from fructose-glucose solutions and for the separation of the disaccharide sucrose from sugar beet or sugar cane syrups.

SMB processes used to separate saccharides use e.g. calcium charged, cross-linked polystyrene resins, anion resins in the bisulfite form (Bechthold M., et al., Chemie Ingenieur Technik, 2010, 82, 65-75), or polystyrenic gel strong acid cation resin in the hydrogen form (Purolite PCR833H) (Purolite, Bala Cynwyd, USA).

Given the continuous mode of operation, the recycling of the mobile phase and also the potential to use large column sizes, SMB systems can in principle be scaled to achieve production volumes of hundreds of tons.

The process step of simulated moving bed chromatography is advantageous in that this process step allows further removal of oligosaccharides being structurally closely related to the desired oligosaccharide.

In an additional and/or alternative embodiment, the process for the purification of 3-fucosyllactose comprises a treatment of the process stream with activated charcoal to remove contaminating substances such as colorants from the process stream.

In additional and/or alternative embodiment, the process for the purification of 3-fucosyllactose comprises at least one step of crystallization or precipitation of 3-fucosyllactose from the cleared process stream. Crystallization or precipitation of 3-fucosyllactose from the process stream may be performed by adding a suitable amount of an organic solvent that is miscible with water to the process stream containing the 3-fucosyllactose. The organic solvent may be selected from the group consisting of $C_1$- to $C_6$-alcohols and $C_1$- to $C_4$-carbon acids.

In an additional and/or alternative embodiment of the process for the purification of the 3-fucosyllactose comprises a step sterile filtration and/or endotoxin removal, preferably by filtration of the process stream through a 3 kDa filter or 6 kDa filter.

In an additional and/or alternative embodiment, the process for the purification of 3-fucosyllactos comprises a step of increasing the concentration of 3-fucosyllactose in the process stream. The concentration of 3-fucosyllactose in the process stream can be increased by subjecting the process stream to vacuum evaporation, reverse osmosis or nanofiltration (e.g. nanofiltration with a nanofiltration membrane having a size exclusion limit of ≤20 Å). Alternatively, crystallized or precipitated 3-fucosyllactose is dissolved in water, to obtain a solution of the 3-fucosyllactose possessing the desired concentration of 3-fucosyllactose.

In an additional and/or alternative embodiment, the resulting process stream is an aqueous solution which contains the 3-fucosyllactose in a concentration of ≥20 g/L, ≥25 g/L, ≥30 g/L, ≥40 g/L, ≥60 g/L, ≥100 g/L, ≥200 g/L or even ≥300 g/L.

In an additional and/or alternative embodiment, the aqueous solution contains the 3-fucosyllactose in a purity of at least 80%, at least 85%, at least 90%, at least 93%, at least 95% or at least 98% with respect to the weight of dry matter/solutes within the solution.

The obtained concentrate containing the purified 3-fucosyllactose can be stored under appropriate conditions.

The process for the purification of 3-fucosyllactose is cost efficient and easy to scale up, making it suitable as a basis for a multi-ton scale manufacturing process.

The process for the purification of 3-fucosyllactose is also advantageous in that the aqueous solution is free of genetically-engineered microorganisms and nucleic acid molecules derived from genetically-engineered microorganisms. In addition, the aqueous solution is free of proteins. The total removal of proteins eliminates the risk of causing allergies to a potential consumer.

The process for the manufacture of the spray-dried powder comprises the step of providing an aqueous solution containing the 3-fucosyllactose.

In an additional and/or alternative embodiment, the aqueous solution contains the 3-fucosyllactose in an amount of at least 20% (w/v), 30% (w/v), 35% (w/v), and up to 45% (w/v), 50% (w/v), 60% (w/v).

In an additional and/or alternative embodiment, the aqueous solution contains the 3-fucosyllactose in a purity of at least 80%, at least 85%, at least 90%, at least 93%, at least 95% or at least 98% with respect to the weight of dry matter/solutes within the solution.

In an additional and/or alternative embodiment, the aqueous solution does not contain genetically-engineered microorganisms, nucleic acid molecules derived from genetically-engineered microorganisms and proteins.

In the process of the manufacture of the spray-dried powder, the aqueous solution containing the 3-fucosyllactose is subjected to spray-drying.

Spray-drying is a method to obtain dry powders, wherein the solution containing the substance of interest (i.e. 3-fucosyllactose) is first sprayed into droplets which are rapidly dried by hot air. Spray-drying is very fast and exposure of the substance to be dried to high temperatures is quite short.

In an additional and/or alternative embodiment, the aqueous solution containing the 3-fucosyllactose that has been purified from a fermentation broth or process stream is spray-dried at a nozzle temperature of at least 110° C., preferably at least 120° C., more preferably at least 125° C., and less than 150° C., preferably less than 140° C. and more preferably less than 135° C.

In an additional and/or alternative embodiment, the aqueous solution containing the 3-fucosyllactose that has been purified from a fermentation broth or process stream is spray-dried at an outlet temperature of at least 60° C., preferably at least 65° C., and less than 80° C., preferably less than 70° C. In a particularly preferred embodiment, the aqueous solution containing the 3-fucosyllactose is spray-dried at a nozzle temperature of about 68° C. to about 70° C.

The spray-drying of the aqueous solution containing 3-fucosyllactse provides a powder of low hygroscopy, wherein the 3-fucosyllactose is present in amorphous form, and wherein the particle size is homogeneous.

According to the third aspect, provided is the use of the spray-dried powder containing 3-fucosyllactose that has been purified from a process stream for the manufacture of a nutritional composition. The spray-dried powder consisting essentially of 3-fucosyllactose is suitable for human consumptions and may thus be included into preparations for human consumption such as medicinal formulations, infant formula, dairy drinks or dietary supplements.

According to the fourth aspect, provided are nutritional compositions which contain a spray-dried powder as described in the first aspect of as manufactured according to the second aspect.

In an additional and/or alternative embodiment, the nutritional composition contains at least one additional HMO which is not 3-fucosyllactose. The at least one additional HMO may be a neutral HMO, preferably selected from the group consisting of 2'-fucosyllactose (2'-FL), lacto-N-tetraose (LNT), lacto-N-neotetraose (LNnT), and lacto-N-fucopentaose I (LNFPI). In an additional and/or alternative embodiment, the at least one additional HMO may be a sialylated HMO, preferably selected from the group consisting of 3'-sialyllactose (3'-SL), 6'-sialyllactose (6'-SL), sialyllacto-N-tetraose (LST)-a, LST-b, LST-c and disialyl-lacto-N-tetraose (DSLNT).

In an additional and/or alternative embodiment, the nutritional composition includes a mixture consisting essentially of Neu5Ac, 2'-FL, 3-FL, LNT, LNnT, LNFPI, 3'-SL, 6'-SL, sialic acid and L-fucose. A nutritional composition including preferred amounts of each of said compounds is provided in Table 1.

TABLE 1

Composition of an exemplary mixture containing suitable as supplement for infant formulae.

| Compound | Proportion in mix (percentage by weight) | Final concentration in infant formula (g/L) |
| --- | --- | --- |
| 2'-FL | 34 | 2.5 |
| 3-FL | 11 | 0.8 |
| LNT | 20 | 1.5 |
| LNnT | 2 | 0.15 |
| LNFPI | 13 | 1.0 |
| 3'-SL | 3 | 0.2 |
| 6'-SL | 4 | 0.3 |
| Neu5Ac | 8 | 0.6 |
| L-Fucose | 5 | 0.4 |
| Total | 100 | 7.45 |

The composition according to the second column in Table 1 is of particular advantage for supplementing infant formula such that the final infant formula for direct consumption may contain the compounds of the mixture in concentrations as speck fled in the third column of Table 1.

In an additional and/or alternative embodiment, the nutritional composition contains one or more additional ingredients. Said one or more additional ingredients are selected from the group consisting of oil, fat and fatty acids (such as olive oil, sunflower oil, coconut oil, nut oil, rapeseed oil, palm oil, flaxseed oil, fish oil, linolenic acid, soy-bean oil, etc.), carbohydrates (such as glucose, fructose, lactose, maltodextrin, starch, sucrose, inositol, etc.) proteins (from skim milk, whey, casein (derived from any domesticated dairy animals), or soy bean), vitamins (A, B1, B2, B5, B6, B12, C, D, E, K, biotin, folic acid, niacin, choline) minerals and trace elements (sodium, potassium, chloride, calcium, phosphorus, magnesium, iron, zinc, manganese, fluoride, selenium, iodine, copper).

In a preferred embodiment the nutritional composition containing the spray dried human milk oligosaccharides or the mixture of human milk oligosaccharides or the mixture of human milk oligosaccharides with functional monosaccharides or the mixture of human milk oligosaccharides with other fibers is an infant formula that meets the compositional requirements set forth in Regulation (EU) 2016/127 and/or in the Code of Federal Regulations (USA) Title 21 107.100 (nutrient specifications). Representative compositions of infant formulas are specified in Tables 2 and 3.

TABLE 2

Components of an exemplary infant formula.

| Infant formula: | Skimmed milk |
| --- | --- |
| | Vegetable oils (palm oil, rapeseed oil, sunflower oil) |
| | Human milk oligosaccharides |
| | 3-fucosyllactose |
| | Skimmed milk powder |
| | Oil of *Mortierella alpine* |
| | Fish oil |
| | Calcium carbonate |
| | Potassium chloride |
| | Vitamin C |
| | Sodium chloride |
| | Vitamin E |
| | Iron acetate |
| | Zinc sulfate |
| | Niacin |
| | Calcium-D-panthothenate |
| | Copper sulfate |
| | Vitamin A |
| | Vitamin B1 |
| | Vitamin B6 |
| | Magnesium sulfate |
| | Potassium iodate |
| | Folic acid |
| | Vitamin K |
| | Sodium selenite |
| | Vitamin D |

TABLE 3

Composition of an exemplary infant formula. The final concentration is based on a preparation of 13.5 g of the powder in 90 ml of water.

| | | per 100 g powder | per 100 ml infant formula |
| --- | --- | --- | --- |
| Energy | kJ | 2094-2145 | 283 |
| | kcal | 500-512 | 67-68 |
| Fats, hereof: | g | 24.2-26.2 | 3.3-3.5 |
| saturated fatty acids | g | 8.7-9.4 | 1.2-1.3 |
| monounsaturated fatty acids | g | 10.4 | 1.4 |
| polyunsaturated fatty acids | g | 5.5-5.9 | 0.7-0.8 |
| Carbohydrates hereof: | g | 56-58 | 7.4-7.9 |
| Sugars hereof: | g | 44-56 | 6-7.4 |
| Lactose | g | 44-56 | 6-7.4 |
| Neu5Ac | mg | 440 | 60 |
| L-fucose | mg | 300 | 40 |
| HMOs Hereof | g | 4.22-4.81 | 0.57-0.65 |
| 2'-FL | g | 1.85-2.22 | 0.25-0.30 |
| 3-FL | mg | 555.56-592.6 | 75-80 |
| LNT | g | 1.11 | 0.15 |
| LNnT | mg | 0-111.11 | 0-15 |
| LNPF-I | mg | 0-740.74 | 0-100 |
| 3'-SL | mg | 148.15-170.37 | 20-23 |
| 6'-SL | mg | 207.4-222.22 | 28-30 |
| Protein | g | 11.11-11.85 | 1.5-1.6 |
| Salt | g | 0.47-0.59 | 0.06-0.08 |
| Vitamins | | | |
| Vitamin A | μg | 357-358 | 47.3-48.2 |
| Vitamin D | μg | 7.8 | 1.05 |
| Vitamin E | mg | 8.15 | 1.1 |
| Vitamin K | μg | 43.7-44.4 | 5.9-6.0 |
| Vitamin C | mg | 115-118 | 15-16 |
| Vitamin B1 | mg | 0.51-0.60 | 0.068-0.079 |
| Vitamin B2 | mg | 1.3-1.7 | 0.18-0.23 |
| Niacin | mg | 3.63 | 0.49 |
| Vitamin B6 | μg | 526-600 | 71-81 |
| Folic acid | μg | 160-164 | 21.6-21.7 |
| Vitamin B12 | μg | 1.7-1.9 | 0.23-0.25 |
| Biotin | μg | 22-30 | 3.0-3.9 |
| Panthothenic acid | mg | 4.6-5.4 | 0.62-0.72 |
| Minerals | | | |
| Sodium | mg | 187-236 | 25.3-31.2 |
| Potassium | mg | 673-675 | 88.8-91.2 |
| Chloride | mg | 327-333 | 43.1-44.9 |
| Calcium | mg | 460-504 | 62.1-66.5 |
| Phosphorous | mg | 335-352 | 45.2-46.5 |
| Magnesium | mg | 49.3-56.3 | 6.66-7.43 |
| Iron | mg | 4.15 | 0.56 |
| Zinc | mg | 3.7-3.8 | 0.49-0.51 |
| Copper | μg | 274 | 37 |
| Manganese | μg | 96.3 | 13 |
| Fluoride | μg | 30.4-32.6 | 4.1-4.4 |
| Selenium | μg | 11.1-12.3 | 1.5-1.6 |
| Iodine | μg | 101.5-103.7 | 13.7-14 |

In an additional and/or alternative embodiment, the nutritional composition also contains microorganisms, preferably probiotic microorganisms. For infant food applications, the preferred microorganisms are derived from or can be found in the microbiome of a healthy human. Preferably, but with no limitations, the microorganisms are selected from the genera *Bifidobacterium, Lactobacillus, Enterococcus, Streptococcus, Staphylococcus, Peptostreptococcus, Leuconostoc, Clostridium, Eubacterium, Veilonella, Fusobacterium, Bacterioides, Prevotella, Escherichia, Propionibacterium* and *Saccharomyces*. In an additional and/or alternative embodiment, the microorganism is selected from the group consisting of *Bifidobacterium adolescentis, B. animalis, B. bifidum, B. breve, B. infantis, B. lactis, B. longum; Enterococcus faecium; Escherichia coli; Klyveromyces marxianus; Lactobacillus acidophilus, L. bulgaricus, L. casei, L. crispatus, L. fermentum, L. gasseri, L. helveticus, L. johnsonii, L. paracasei, L. plantarum, L. reuteri, L. rhamnosus, L. sali-*

*varius, L. sakei; Lactococcus lactis* (including but not limited to the subspecies *lactis, cremoris* and *diacetylactis*); *Leuconostoc mesenteroides* (including but not limited to subspecies *mesenteroides*); *Pedicoccus acidilactici, P. pentosaceus; Propionibacterium acidipropionici, P. freudenreichii* ssp. *shermanii; Staphylococcus carnosus*; and *Streptococcus thermophilus.*

In addition to the combination living organisms, the nutritional composition can also include dead cell cultures. In the field of probiotics, killed cell cultures are sometimes used (e.g. tyndalized bacteria). These killed cultures may provide proteins, peptides, oligosaccharides, cell outer wall fragments and natural products, leading to the short-term stimulation of the immune system.

Including probiotic microorganisms in the nutritional composition, especially in the presence of HMOs, is particularly advantageous in that it also promotes the establishment of a healthy gut microbiome.

In an additional and/or alternative embodiment, the nutritional composition also includes prebiotics such as galacto-oligosaccharides (GOS), fructo-oligosaccharides (FOS), inulin or combinations thereof.

The nutritional composition is present in solid form including, but not limited to, powders, granules, flakes, pellets or combinations thereof.

In an additional embodiment, the nutritional composition is selected from the group consisting of medicinal formulations, infant formulas, dairy drinks and dietary supplements.

As a medicinal formulation, the nutritional composition may be used to improve cognitive performance, especially for improving attention, learning and/or memory.

The present invention will be described with respect to particular embodiments and with reference to drawings, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", as used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification do not necessarily refer always to the same embodiment. Furthermore, the particular features, structures or characteristics may be combined in any suitable manner, as would be apparent to one of ordinary skill in the art from this disclosure, in one or more embodiments.

Similarly, it should be appreciated that in the description of representative embodiments of the invention, various features of the invention are sometimes grouped together in a single embodiment, figure, or description thereof for the purpose of streamlining the disclosure and facilitating the understanding of one or more of the various inventive aspects. This method of disclosure is not to be interpreted as reflecting an intention that the claimed invention requires more features than are expressly listed in each claim. Rather, as the following claims reflect, inventive aspects may require fewer than all the features of any foregoing disclosed embodiment. Thus, the claims following the detailed description are hereby expressly incorporated into this detailed description, with each claim standing on its own as a separate embodiment of this invention.

Furthermore, whereas some embodiments described herein include some but not other features included in other embodiments, combinations of features of different embodiments are meant to be within the scope of the invention, and form different embodiments, as would be understood by those familiar with the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order to facilitate the understanding of the description and drawings.

The invention will now be described by a detailed description of several embodiments of the invention. It is clear that other embodiments of the invention can be configured according to the knowledge of persons skilled in the art without departing from the true spirit or technical merit of the invention, the invention being limited only by the terms of the appended claims.

Example 1: Purification of 2'-Fucosyllactose from Fermentation Broth

Production of 2'-fucosyllactose by fermentation using a genetically modified *E. coli* strain was performed as described in European patent application No. 16 196 486.1. The 2'-fucosyllactose was purified from the fermentation broth by filtration, ion exchange chromatography, nanofiltration, diafiltration or electrodialysis, and treatment with charcoal as described in WO 2015/106943 A1. The resulting solution containing 2'-fucosyllactose was subjected to spray-drying to obtain a stable solid product.

Example 2: Purification of 3-Fucosyllactose from Fermentation Broth

3-Fucosyllactose was produced by fermentation using a genetically modified E. coli strain as described in European patent application No. 16 196 486.1.

The cells were separated from the culture medium by ultrafiltration (0.05 μm cut-off) (CUT membrane technology, Erkrath, Germany) followed by a cross-flow filter with a MWCO of 150 kDa (Microdyn-Nadir, Wiesbaden, Germany). The cell-free fermentation medium containing about 30 g/L 3-fucosyllactose, was passed over a strong cationic ion exchanger (Lewatit S 2568 (Lanxess, Cologne, Germany) in $H^+$ form to remove positive charged contaminants. Afterwards the solution was set to pH 7.0 using sodium hydroxide and applied to an anionic ion exchanger (Lewatit S6368 A, Lanxess) in the chloride form. Both ion exchangers were used in 200 L volume. After a second filtration (150 kDa; Microdyn-Nadir, Wiesbaden, Germany) the particle free solution was concentrated 5-fold by nanofiltration using a Filmtech NF270 membrane (Dow, Midland, USA) and 2.5-fold by vacuum evaporation. The concentrated solution and a conductivity of about 15 mS $cm^{-1}$ was filtrated (10 kDa; Microdyn-Nadir, Wiesbaden, Germany), clarified by activated carbon charcoal (CAS: 7440-44-0, Carl Roth, Karlsruhe, Germany) and deionized by electrodialysis. Therefor a PC-Cell BED 1-3 electrodialysis apparatus (PC-Cell, Heusweiler, Germany) with a PC-Cell E200 membrane stack was used containing the following membranes: cation exchange membrane CEM: PC SK and anion membrane AEM: PCAcid60. 0.25 M Sulphamic acid was used as electrolyte in the process. For reduction of brownish coloring caused by Maillard-reactions and aldol products originating from the fermentation process, a second round of ion exchange chromatography was performed using the same ion exchange material as aforementioned in $Na^+$ and $Cl^-$ form, however in a volume of 50 L. After concentrating the sugar solution by evaporation, again the conductivity was reduced from 4 mS $cm^{-1}$ to 0.4 mS $cm^{-1}$ or less by electrodialysis using the PC-Cell BED 1-3 mentioned previously. For further decolorization the solution was mixed with activated charcoal (CAS: 7440-44-0, Carl Roth, Karlsruhe, Germany) and a nearly colorless solution was obtained by filtration.

Example 3: Purification of Lacto-N-Tetraose from Fermentation Broth

Fermentative production of Lacto-N-tetraose was conducted using a genetically modified E. coli BL21 (DE3) ΔlacZ strain, with genomically integrated genes essential for the in vivo synthesis of Lacto-N-tetraose., namely, a N-acetylglucosamine glycosyltransferase (IgtA from Neisseria meningitidis MC58), a β-1,3-galactosyltransferases (wbdO from Salmonella enterica subsp. salamae serovar Greenside), lacY from E. coli K12, the UDP-glucose-4-epimerase galE, and the UTP-glucose-1 phosphat uridyltransferase galU, both from E. coli K12. In addition, the galS gene encoding a glucosamine-6-phosphate synthase was overexpressed. For the fermentative production of Lacto-N-tetraose the strain was grown in a defined mineral salts medium comprising 2% glucose as carbon source. Antifoam was added when needed. The pH was controlled using a 25% ammonia solution. Lactose was added stepwise to a final concentration of 15 mM from a 216 g $l^{-1}$ lactose stock, the lactose concentration in the culture medium was held constant throw-out the fermentation process. Residual lactose and Lacto-N-triose II, accumulation during the process as by-product, was hydrolyzed by a second E. coli strain that was added to the fermenter. This strain expressed a functional beta-lactamase, a beta-N-acetylhexosaminidase (bbhI from Bifidobacterium bifidum JCM1254), and a functional gal-operon for degradation of monosaccharides (EP 2 845 905 A).

Cells were separated from the fermentation broth, and the lacto-N-tetraose containing fluid was purified to a purity of 75-80%, determined by mass balance, according to the procedure described in example 2.

Contaminating carbohydrate by-products resulting from inefficient enzymatic degradation and metabolization were removed by chromatography using a simulated moving bed (SMB) chromatography, according to WO 2015/049331. Alternatively, the lacto-N-tetraose was purified by crystallization with isopropanol. For crystallization the lacto-N-tetraose containing solution was concentrated by evaporation to a concentration of 20% and spray-dried. Using a NUBILOSA LTC-GMP spray dryer (NUBILOSA, Konstanz, Germany) the solution was passed under nitrogen flow through the spray dryers nozzles with an inlet temperature of 130° C. while the product flow was controlled to maintain an outlet temperature of 67° C. to 68° C.

The solid material was added to a mixture of isopropanol and water (3:1 (vol/vol)) in a ratio of 1 kg powder in 12 L isopropanol/water. The suspension was stirred vigorously, then the insoluble lacto-N-tetraose was filtrated and dried at 40° C. Starting with a 73-89% pure material, the crystallized Lacto-N-tetraose was purified to about 95%, with a recovery of 85%. The sugar was dissolved in water to a concentration of 25% and passed sequentially through a 6 kDa filter (Pall Microza ultrafiltration module SIP-2013, Pall Corporation, Dreieich, Germany) and a 0.2 μm sterile filter. Solid material was obtained by spray drying the sterile material under the conditions described above.

Example 4: Purification of 3'- and 6'-Sialyllactose from Fermentation Broth

For production of 3'-sialyllactose and 6'-sialyllactose recombinant E. coli BL21 (DE3) ΔlacZ strains were used. The strains had common genetic modifications: chromosomal, constitutive expression of the glucosamine-6-phosphate synthase GlmS from E. coli, the N-acetylglucosamin2-epimerase Slr1975 from Synechocystis sp., the glucosamine 6-phosphat N-acetyltransferase Gna1 from Saccharomyces cerevisiae, the phosphoenolpyruvate synthase PpsA from E. coli, the N-acetylneuraminate synthase NeuB, and the CMP-sialic acid synthetase NeuA, the latter both from Campylobacter jejuni. Additionally, the genes encoding the lactose permease LacY from E. coli, cscB (sucrose permease), cscK (fructokinase), cscA (sucrose hydrolase), and cscR (transcriptional regulator) from E. coliW, and a functional gal-operon, consisting of the genes galE (UDP-glucose-4-epimerase), galT (galactose1-phosphate uridylyltransferase), galK (galactokinase), and galM (galactose-1-epimerase) from E. coli K12 were integrated into the genome of the BL21 strain, and constitutively expressed.

The strain synthesizing 3'-sialyllactose harbors the alpha-2,3-sialyltransferase gene from Vibrio sp. JT-FAJ-16, while the 6'-sialyllactose producing strain contains the alpha-2,6-sialyltransferase plsT6 from Photobacterium leiognathi JT-SHIZ-119.

The sialyllactose producing strains were grown in a defined mineral salts medium containing 2% sucrose as carbon source. The sucrose feed (500 g $l^{-1}$), fed in the fed-batch phase, was supplemented with 8 mM MgSO4, 0.1 mM CaCl$_2$), trace elements, and 5 g l$^{-1}$ NH$_4$Cl.

For sialyllactose formation, a lactose feed of 216 g l$^{-1}$ was employed. The pH was controlled by using ammonia solution (25% v/v). Fed batch fermentation was conducted at 30° C. under constant aeration and agitation. In order to remove residual lactose at the end of the fermentation, β-galactosidase was added to the fermentation vessel. The resulting monosaccharides were metabolized by the production strain.

The cell-free liquid was then deionized by ion exchange chromatography. First, cationic contaminants were removed on a strong cationic exchanger in a volume of 200 L (Lewatit S 2568 (Lanxess, Cologne, Germany) in H$^+$ form. Using NaOH the pH of the obtained solution was set to 7.0. In a second step, anionic ions and undesired colorants were removed from the solution using the strong anionic exchanger Lewatit S 6368 S (Lanxess, Cologne, Germany) in the chloride form. The ion exchanger had a bed volume of 200 L. Using a second filtration step on the cross-flow filter (150 kDa cut-off) (Microdyn-Nadir, Wiesbaden, Germany), precipitates originating from acidifying the solution were removed. For concentration of the sugar, the solution was nanofiltrated on a Dow FILMTECH NF270-4040 (Inagua, Mönchengladbach, Germany), or, alternatively on a Trisep 4040-XN45-TSF Membrane (0.5 kDa cut-off) (Microdyn-Nadir, Wiesbaden, Germany). Using the latter, the monosaccharide N-acetylglucosamine, originating from the fermentation process and contaminating the sialyllactose solution, was separated from the product. The concentrated sialyllactose solution was then treated with activated charcoal (CAS: 7440-44-0, Carl Roth, Karlsruhe, Germany) to remove colorants such as Maillard reaction products and aldol reaction products. In order to separate the sialyllactose from by-products that originate from the fermentation process like sialic acid and N-acetylglucosmine, the solution was filtrated on with a 1 kDa cut-off membrane GE4040F30 (GE water & process technologies, Ratingen, Germany), and diafiltrated to a conductivity of 0.6 to 0.8 mS cm$^{-1}$. The diluted solution was concentrated on a rotary evaporator to a concentration of about 300 g/L. In a final chromatographic separation other contaminating sugars, like di-sialyllactose were removed. Therefor the concentrated solution was applied to a weak anion ion exchange resin in the acetate form (Amberlite FPA51, Dow Chemical, Michigan, USA). While the sialyllactose rarely binds to the resin, the di-sialyllactose is adsorbed. Thus, the sialyllactose is eluted with 10 mM ammoniumacetat, while the di-sialyllactose is eluted with 1 M ammoniumacetat. For removal of the ammoniumacetat, the sialyllactose was precipitated with a 10-fold excess of ethanol. The solid fraction was filtrated and dried.

The product was finalized by passing a 20% sialyllactose solution sequentially through a 6 kDa filter (Pall Microza ultrafiltration module SIP-2013, Pall Corporation, Dreieich, Germany) and a 0.2 µm sterile filter.

A part of the solution was spray dried using a Büchi spray dryer (Büchi Mini Spray Dryer B-290) (Büchi, Essen, Germany), applying the following parameters: Inlet-temperature: 130° C., Outlet temperature 67° C.-71° C., gasflow 670 L/h, aspirator 100%.

The spray-dried 6'-sialyllactose had a purity of 91%, while the 3'-sialyllactose material had a purity of 93%.

Example 5: Preparations of HMO Mixtures

Mixtures of HMOs were prepared from solid products. Therefor the single HMOs were spray-dried and the powder were mixed. HMO-Mix I contained 2'-fucosyllactose and lacto-N-tetraose in a ratio of 70% to 30%; HMO-Mix II contained 2'-fucosyllactose (52%), 3-fucosyllactose (13%), lacto-N-tetraose (26%), 3'-sialyllactose (4%), and 6'-sialyllactose (5%). The mixed powders were solved in water to a solution of 20% sugar, and spray-died again using the Büchi spray dryer as described in example 4.

Example 6: Characterisation of Spray-Dried Human Milk Oligosaccharides 6.1 Differential Scanning Calorimetry (DSC)

Using differential scanning calorimetry (DSC) on a Mettler Toledo 821e (Mettler Toledo, Giessen, Germany) thermal events of spray-dried human milk oligosaccharides, namely 3-fucosyllactose, 6'-sialyllactose, 3'-sialyllactose, lacto-N-tetraose, and spray-dried mixtures of human milk oligosaccharides, a mixture (HMO-Mix I) of 2'-fucosyllactose/lacto-N-tetraose, and a mixture (HMO Mix II) of 2'-fucosyllactose, 3-fucosyllactose, lacto-N-tetraose, 6'-sialyllactose, 3'-sialyllactose, respectively, were determined.

A Mettler Toledo 821e (Mettler Toledo, Giessen, Germany) was used to determine thermal events of the spray-dried products (glass transition temperature (Tg), further exo- and endothermic events).

Approximately 25 mg of the spray-dried human milk oligosaccharides were analyzed in crimped Al-crucibles (Mettler Toledo, Giessen, Germany). The samples were cooled to 0° C. with 10 K/min and reheated to 100° C. with a scanning rate of 10 K/min. After cooling down the samples to 0° C. in a second heating cycle, the samples were reheated to 150° C. The midpoint of the endothermic shift of the baseline during the heating scan was taken as glass transition temperature (Tg). Exothermic and endothermic peaks are reported by means of the peak temperature and the normalized energy of the event.

The first heating scan in all samples showed a main glass transition event in the total heat flow, as evidenced by a main step transition in the range of approximately 48-58° C., in most of the samples, the major glass transition event observed in the first heating scan reoccurred in the second heating scan. The results of the DSC analyses are summarized in table 4.

TABLE 4

Thermal events of HMOs as determined by differential scanning calorimetry

| Sample | 1$^{st}$ heating scan Tg [° C.] | 2$^{nd}$ heating scan Tg [° C.] |
|---|---|---|
| 3-fucosyllactose | 57.6 | 59.9 |
| lacto-N-tetraose | 49.9 | 79.4 |
| 6'-sialyllactose | 47.6 | 49.6 |
| 3'-sialyllactose | 48.8 | 54.3 |
| 2'-fucosyllactose/lacto-N-tetraose | 56.3 | 59 |
| HMO Mix | 54.2 | 55.6 |

For 3-fucosyllactose an endothermal relaxation peak after Tg in the first heating scan was detected. For lacto-N-tetraose a much higher Tg of about 79° C. was detected in the 2$^{nd}$ heating scan compared to that of the other samples. This might be caused by an endothermal event during the first heating scan at about 89° C. (−6.04 J/g). Like for 3-fucosyllactose, also for 6'-sialyllactose an endothermal relaxation peak was detected after Tg, however, in this sample additionally an endothermal event occurred at 77° C. (−0.22 J/g). No endothermal events were detected for the 3'-sialyllactose and the HMO-Mix I, for HMO-Mix II the endothermal event during the 1st heating scan was at 79° C. (0.34 J/g).

6.2 X-Ray Powder Diffraction (XRD)

Wide angle X-ray powder diffraction (XRD) was used to study the morphology of lyophilized products. The X-ray diffractometer Empyrean (Panalytical, Almelo, The Netherlands) equipped with a copper anode (45 kV, 40 mA, $K_{\alpha 1}$ emission at a wavelength of 0.154 nm) and a PIXcel3D detector was used. Approximately 100 mg the spray-dried samples were analyzed in reflection mode in the angular range from 5-45° 2θ, with a step size of 0.04° 2θ and a counting time of 100 seconds per step.

Figure 2:
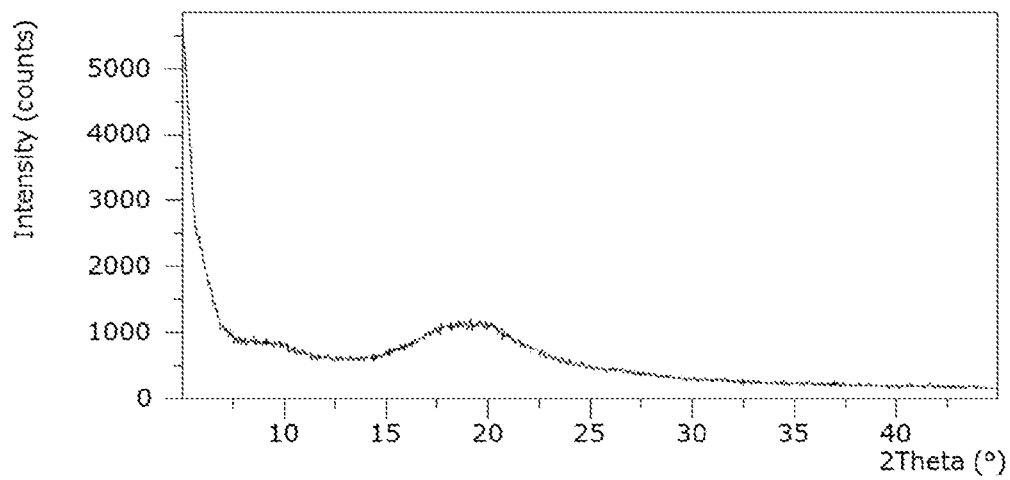
FIG. 2 shows a graph illustrating the results of a X-ray powder diffraction of spray-dried lacto-N-tetraose.
Figure 3:
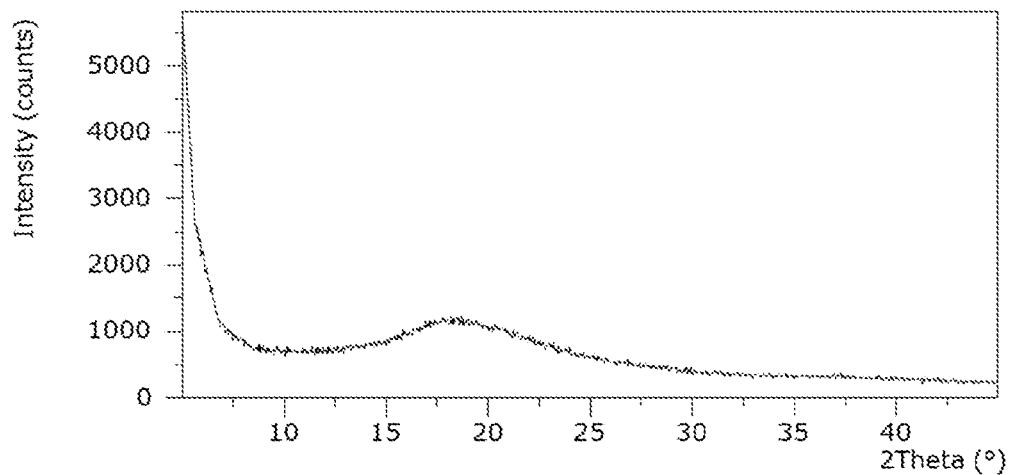
FIG. 3 shows a graph illustrating the results of a X-ray powder diffraction of spray-dried 6'-sialyllactose.
Figure 4:
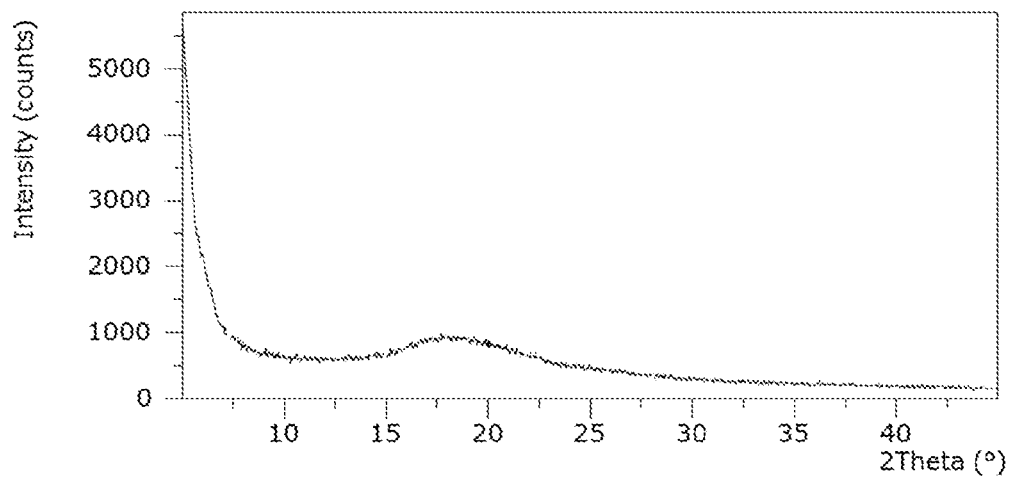
FIG. 4 shows a graph illustrating the results of a X-ray powder diffraction of spray-dried 3'-sialyllactose.
Figure 5:
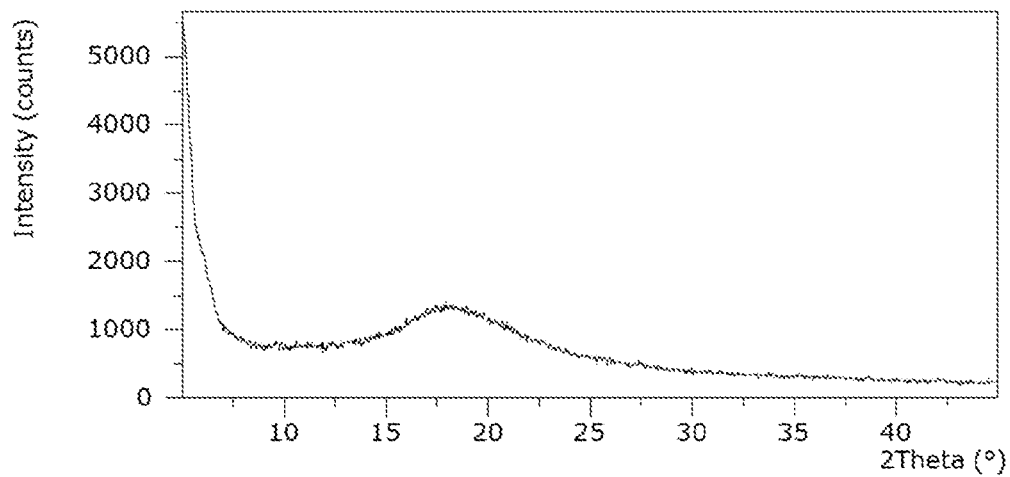
FIG. 5 shows a graph illustrating the results of a X-ray powder diffraction of a spray-dried mixture of 2'-fucosyllactose and lacto-N-tetraose.
Figure 6:
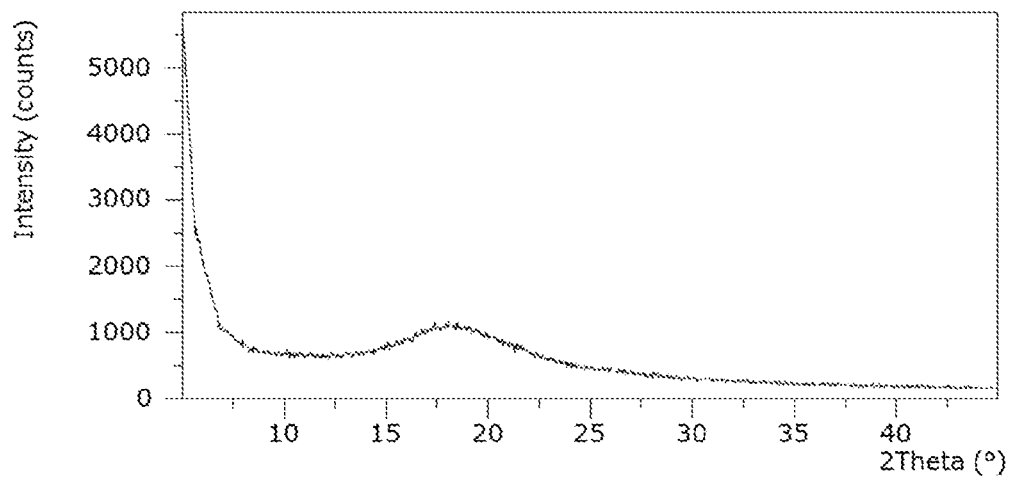
FIG. 6 shows a graph illustrating the results of a X-ray powder diffraction of a spray-dried mixture of 2'-fucosyllactose, 3-fucosyllactose, lacto-N-tetraose, 3'-sialyllactose, and 6'-sialyllactose.

All singular oligosaccharides as well as the HMO Mixes I and II showed a fully amorphous state (FIGS. 1 to 6). For lacto-N-tetraose a second (amorphous) signal was detected around 9-10°.

6.3 Laser Diffraction

The powder particle size was assessed by laser diffraction. The system detects scattered and diffracted light by an array of concentrically arranged sensor elements. The software-algorithm is then approximating the particle counts by calculating the z-values of the light intensity values, which arrive at the different sensor elements. The analysis was executed using a SALD-7500 Aggregate Sizer (Shimadzu Corporation, Kyoto, Japan) quantitative laser diffraction system (qLD).

A small amount (spatula tip) of each sample was dispersed in 2 ml isooctane and homogenized by ultrasonication for five minutes. The dispersion was transferred into a batch cell filled with isooctane and analyzed in manual mode.

Data acquisition settings were as follows: Signal Averaging Count per Measurement: 128, Signal Accumulation Count: 3, and Interval: 2 seconds.

Prior to measurement, the system was blanked with isooctane. Each sample dispersion was measured 3 times and the mean values and the standard deviation are reported. Data was evaluated using software WING SALD II version V3.1. Since the refractive index of the sample was unknown, the refractive index of sugar (disaccharide) particles (1.530) was used for determination of size distribution profiles. Size values for mean and median diameter are reported.

The mean particle sizes for all samples were very similar, slightly lower values were measured for HMO-Mix II. The particle size characteristics are summarized in Table 5. In addition, the particle size distribution showed the presence of one main size population for all of the samples.

ganisms and nucleic acid molecules derived from genetically-engineered microorganisms, and
wherein the nutritional composition further comprises at least one probiotic microorganism.

2. The nutritional composition of claim 1, wherein the spray-dried powder comprises at least 85%-wt 3-fucosyl-lactose.

3. The nutritional composition of claim 1, wherein the 3-fucosyllactose is present in amorphous form.

4. The nutritional composition of claim 1, wherein the spray-dried powder comprises ≤7%-wt. of water.

5. A process for the manufacture of the spray-dried powder of the nutritional composition of claim 1, wherein the process comprises
 a) purifying the 3-fucosyllactose from a fermentation broth;
 b) providing an aqueous solution containing the 3-fucosyllactose of a); and
 c) subjecting the solution of b) to spray-drying to obtain the spray-dried powder.

6. The process according to claim 5, wherein the purifying the 3-fucosyllactose from a fermentation broth a) includes one or more of
 i) removing the microbial cells from the fermentation broth to obtain a cleared process stream;
 ii) subjecting the cleared process stream to at least one ultrafiltration;
 iii) treating the cleared process stream at least one time with a cation exchange resin and/or at least one time with an anion exchange resin;
 iv) subjecting the cleared process stream to at least one nanofiltration and/or diafiltration;
 v) subjecting the cleared process stream to at least one electrodialysis;
 vi) treating the cleared process stream at least one time with activated charcoal; and/or
 vii) subjecting the cleared process stream at least one time to a crystallization and/or precipitation.

7. The process according to claim 5, wherein the aqueous solution comprises the 3-fucosyllactose in an amount of at least 20% (w/v), optionally at least 30% (w/v), and optionally at least 35% (w/v), and up to 45% (w/v), optionally at least 50% (w/v), and optionally at least 60% (w/v).

8. The process according to claim 5, wherein the aqueous solution comprising the 3-fucosyllactose is spray dried at a nozzle temperature of at least 110° C., optionally at least 120° C., optionally at least 125° C., and less than 150° C., optionally less than 140° C., and optionally less than 135° C.

TABLE 5

Particle size of HMOs as determined by laser diffraction

| Size | 3-fucosyl-lactose | lacto-N-tetraose | 6'-sialyllactose | 3'-sialyllactose | HMO-Mix I | HMO Mix II |
|---|---|---|---|---|---|---|
| Mean [nm] | 119.2 ± 0.5 | 117.3 ± 0.7 | 113.8 ± 1.5 | 115.4 ± 0.6 | 113.1 ± 0.3 | 97.3 ± 5.3 |
| Median [nm] | 141.3 ± 0.0 | 141.3 ± 0.0 | 141.3 ± 0.0 | 121.9 ± 16.7 | 141.3 ± 0.0 | 112.2 ± 0.0 |

The invention claimed is:

1. A nutritional composition comprising a spray-dried powder,
 wherein the spray-dried powder comprises at least 80%-wt. 3-fucosyllactose which has been produced by microbial fermentation,
 wherein the spray-dried powder contains ≤15%-wt. of water and is free of genetically-engineered microor- 9. The process according to claim 5, wherein the aqueous solution comprising the 3-fucosyllactose is spray-dried at an outlet temperature of at least 60° C., optionally at least 65° C., and less than 80° C., optionally less than 70° C.

10. The nutritional composition of claim 1, wherein the nutritional composition is an infant formula.

11. The nutritional composition of claim 1, further comprising at least one additional HMO, wherein said at least one additional HMO is a neutral HMO or a sialylated HMO.

12. The nutritional composition of claim 11 wherein the at least one neutral HMO is selected from the group consisting of 2'-fucosyllactose, lacto-N-tetraose, lacto-N-neotetraose and lacto-N-fucopentaose I.

13. The nutritional composition of claim 11, wherein the at least one sialylated HMO is selected from the group consisting of 3'-sialyllactose, 6'-sialyllactose, sialyllacto-N-tetraose (LST)-a, LST-b, LST-c and disialyllacto-N-tetraose.

14. The nutritional composition of claim 2, wherein the spray dried powder comprises at least 90%-wt 3-fucosyllactose.

15. The nutritional composition of claim 2, wherein the spray dried powder comprises at least 98%-wt 3-fucosyllactose.

16. The nutritional composition of claim 1, wherein the spray dried powder comprises ≤10%-wt. of water.

17. The nutritional composition of claim 1, wherein the spray dried powder consists essentially of 3-fucosyllactose.

* * * * *